United States Patent
Igarashi et al.

(12)

(10) Patent No.: US 6,337,382 B1
(45) Date of Patent: Jan. 8, 2002

(54) PREPARATION OF SILANOL-CONTAINING ORGANOSILICON COMPOUNDS

(75) Inventors: Minoru Igarashi; Keiji Shibata, both of Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/570,553

(22) Filed: May 12, 2000

(30) Foreign Application Priority Data

May 12, 1999 (JP) .......................................... 11-131645

(51) Int. Cl.[7] ................................................ C08G 77/08
(52) U.S. Cl. .......................................... 528/23; 528/12
(58) Field of Search ....................................... 528/12, 23

(56) References Cited

U.S. PATENT DOCUMENTS 5,401,821 A * 3/1995 Geck et al.

* cited by examiner

*Primary Examiner*—Robert Dawson
*Assistant Examiner*—Marc S. Zimmer
(74) *Attorney, Agent, or Firm*—Birch, Stewart, Kolasch & Birch, LLP

(57) ABSTRACT

Silanol group-containing organosilicon compounds having a low average degree of polymerization are prepared in an efficient and inexpensive manner by adding water at pH 1–5 to an organooxysilane, mixing them, thus forming a hydrolyzed organooxysilane mixture, and adding a mono- and/or di-alkali metal salt of phosphoric acid to the mixture so as to give pH 5–9.

7 Claims, No Drawings

PREPARATION OF SILANOL-CONTAINING ORGANOSILICON COMPOUNDS

This invention relates to a method for preparing silanol group-containing organosilicon compounds from organooxysilanes.

BACKGROUND OF THE INVENTION

Organosilanes and siloxanes having silanol groups in their molecule are known to be effective dispersants for use in the manufacture of silicone rubber compounds. Their dispersing capability tends to increase as the content of hydroxyl groups increases. More particularly, low molecular weight organosilanes and siloxanes having silanol groups have higher hydroxyl contents and hence, higher dispersing capability than high molecular weight ones. Therefore, the low molecular weight organosilanes and siloxanes have the advantage that they are effective as the dispersant even in small amounts, which in turn, is not detrimental to the working of silicone rubber compounds.

Currently, the low molecular weight organosilanes and siloxanes are industrially manufactured by hydrolyzing organochlorosilanes having a chlorine atom at the end of their molecular chain in a weakly alkaline aqueous solution so as to avoid cyclization. This method, however, has the problem that silanol groups undergo condensation reaction with HCl formed by hydrolysis, resulting in a product having a higher molecular weight than the desired organosiloxane or a cyclic product. It is also known that an organochlorosilane is treated with acetic acid to introduce acetoxy before hydrolysis is effected. With this method, however, it is difficult to effect hydrolysis to completion, leaving acetoxy groups in the product. Such organopolysiloxanes are inadequate as the dispersant for use in the manufacture of silicone rubber compounds.

U.S. Pat. No. 3,925,285 discloses a method for synthesizing a low molecular weight, linear, silanol-terminated polyorganosiloxane by reacting hexamethylcyclotrisiloxane with methanol, formic acid, and water. This method is uneconomical since relatively expensive hexamethylcyclotrisiloxane is utilized. The method fails to produce a low molecular weight, linear, silanol-terminated polyorganosiloxane having a degree of polymerization of less than 3. It is impossible to obtain a silanol-containing organosiloxane having a lower molecular weight.

In U.S. Pat. No. 5,057,620, a chlorosiloxane is added dropwise to a water-containing epoxy solvent such as propylene oxide or butylene oxide. This method uses relatively expensive hexamethylcyclotrisiloxane as the reactant, imposing a cost problem. The method also uses a low boiling solvent having the risk of electrostatic ignition, leaving a safety problem.

In U.S. Pat. No. 5,378,788, an alkoxysilane is hydrolyzed with acidic water and neutralized with a metal oxide. This method yields silanol-containing organosiloxanes having an average degree of polymerization of 3 or higher. It is difficult to obtain a silanol-containing organosiloxane having a lower molecular weight.

SUMMARY OF THE INVENTION

An object of the invention is to provide a method for preparing silanol-containing organosilicon compounds having a low molecular weight using a relatively inexpensive organooxysilane as the starting reactant rather than expensive reactants.

It has been found that by adding a specific amount of water at pH 1 to 5 to at least one organooxysilane to effect hydrolysis and then adding a mono- and/or di-alkali metal salt of phosphoric acid thereto, low molecular weight, silanol-containing organosilicon compounds, especially organosilicon compounds containing hydroxyl (or silanol) groups and having an average degree of polymerization of more than 1 to less than 3 (that is, a mixture of silanes and siloxanes) can be produced in an easy, reliable and efficient manner.

The invention provides a method for preparing organosilicon compounds having silanol groups, comprising the steps of:

adding water adjusted at pH 1 to 5 to at least one organooxysilane of the following general formula (1):

$$(R^1O)_a SiR_{4-a} \qquad (1)$$

wherein $R^1$ and R are independently substituted or unsubstituted monovalent hydrocarbon groups, and "a" is an integer of 1 to 4, in an amount of 0.5 to 3 mol per mol of the organooxy group in the organooxysilane, mixing them, thus forming a hydrolyzed organooxysilane mixture, and adding a mono-alkali metal salt of phosphoric acid and/or di-alkali metal salt of phosphoric acid to the mixture.

DESCRIPTION OF THE PREFERRED EMBODIMENT

The method for preparing silanol group-containing organosilicon compounds according to the invention starts with an organooxysilane of the general formula (1).

$$(R^1O)_a SiR_{4-a} \qquad (1)$$

Herein R is selected from substituted or unsubstituted monovalent hydrocarbon groups, preferably having 1 to 10 carbon atoms, more preferably 1 to 8 carbon atoms. Exemplary are alkyl groups such as methyl, ethyl, propyl, butyl and pentyl, cycloalkyl groups such as cyclohexyl, alkenyl groups such as vinyl, allyl and propenyl, aryl groups such as phenyl and tolyl, aralkyl groups such as β-phenylethyl, and substituted ones of these groups in which some or all of the hydrogen atoms attached to carbon atoms are replaced by halogen atoms (e.g., fluorine and chlorine) and cyano groups, such as 3,3,3-trifluoropropyl and cyanoethyl. Of these, methyl, ethyl, vinyl, phenyl and 3,3,3-trifluoropropyl are preferred.

$R^1$ is selected from substituted or unsubstituted monovalent hydrocarbon groups as defined for R, preferably alkyl groups such as methyl and ethyl. Letter "a" is an integer of 1 to 4, and preferably equal to 2. When "a" is 2 or more, the $R^1$ groups may be identical or different.

Illustrative examples of the organooxysilane of formula (1) include dimethoxydimethylsilane, diethoxydimethylsilane, phenylmethyldimethoxysilane, methylvinyldimethoxysilane, trimethylmethoxysilane, trimethylethoxysilane, methyltrimethoxysilane, methyltriethoxysilane, vinyltrimethoxysilane, and phenyltrimethoxysilane.

These organooxysilanes may be used alone or in admixture of two or more.

In the practice of the invention, first of all, acidic water is added to the organooxysilane of formula (1) as hydrolytic water for hydrolyzing the organooxysilane. This hydrolytic water is a component necessary to hydrolyze the organooxysilane and is previously adjusted to pH 1 to 5, preferably pH 3 to 4.5. If the pH is below the range, hydrolytic reaction is immediately followed by rapid condensation reaction to invite a molecular weight increase and formation of cyclic compounds, making it difficult to produce low molecular weight organosilicon compounds having high silanol contents. If the pH is above the range, the catalysis necessary for hydrolysis is not obtained and hydrolysis proceeds no longer. The acids used to adjust the pH of water include inorganic acids such as hydrochloric acid, sulfuric acid, nitric acid and phosphoric acid and organic acids such as formic acid and acetic acid. Acidic water is preferably used in an amount of 0.5 to 3 mol, especially 1 to 1.5 mol per mol of the organooxy group in the organooxysilane. Less amounts of water fail to drive hydrolysis of organooxy groups to completion. If water is used in excess, a noticeable amount of unreacted water is left in the reaction mixture.

Reaction of the organooxysilane with acidic water is generally effected at a temperature of 0 to 70° C., and preferably 20 to 50° C. Since the organooxysilane and acid water do not mix with each other and remain separate as two phases at the initial stage of reaction, agitation is necessary in order to bring them in full contact. As hydrolysis proceeds, water is consumed, an alcohol forms, and the system becomes homogeneous.

The hydrolysis time varies with the pH of hydrolytic water and the type of organooxysilane reactant. For example, when dimethyldimethoxysilane is hydrolyzed with hydrochloric acid water at pH 3.5, a two-phase system forms initially. With the progress of reaction, the system becomes homogeneous. It takes about 2 minutes until the system becomes homogeneous. At this point, low molecular weight, silanol-containing organosilicon compounds such as dihydroxydimethylsilane and dihydroxytetramethyldisiloxane are prevalent. Where compounds of greater chain length are desired, agitation is further continued to effect condensation reaction. Therefore, the hydrolysis time is selected so as to provide the desired chain length. An appropriate hydrolysis time can be determined without undue experimentation.

According to the invention, after the organooxysilane is hydrolyzed in this way, a mono-alkali metal salt of phosphoric acid and/or a di-alkali metal salt of phosphoric acid is added to the hydrolysate mixture. The mono- or di-alkali metal salt of phosphoric acid serves as a reaction stopper. By adding the phosphoric salt, the hydrolysate mixture is preferably adjusted to pH 5 to 9. By neutralizing the hydrolysate mixture with the phosphoric salt, silanols of short chain length can be readily obtained. The resulting short chain silanols have a good stability of chain length with the lapse of time.

Examples of the mono-alkali metal salt of phosphoric acid include $KH_2PO_4$ and $NaH_2PO_4$ and examples of the di-alkali metal salt of phosphoric acid include $K_2HPO_4$ and $Na_2HPO_4$. It is preferable to use a mixture of mono- and di-alkali metal salts of phosphoric acid, more preferably in a weight ratio of from 0.1:10 to 10:0.1. These salts are generally used in aqueous solution form although solid salts can be added without dissolving in water. The amount of the phosphoric salt added varies with its type and the concentration when added as an aqueous solution. An appropriate amount of the phosphoric salt is to adjust the hydrolysate mixture at pH 5 to 9, especially above pH 5 to pH 7.

After the phosphoric salt is added, there sometimes precipitates a salt which does not dissolve in the hydrolyzate mixture. Such a precipitate can be readily removed as by filtration.

After the phosphoric salt is added, the unreacted reactant, alcohol by-product and water are optionally removed from the reaction system by well-known purifying means, for example, vacuum distillation.

The above-described method yields a mixture of silanol group-containing silanes and siloxanes, specifically a mixture of silanes of the formula: $(HO)_aSiR_{4-a}$ and siloxanes terminated with a OH group and having 1 to 15 silicon atoms, especially 1 to 10 silicon atoms and represented by the average compositional formula: $R_{4-a}SiO_{a/2}$, for example, a mixture of $(HO)_2SiR_2$ and $HO(SiR_2O)_nH$ when a=2. In the formulae, R is as defined above and n is a number of at least 1, preferably 1 to 15, and especially 1 to 10.

According to the invention, there can be obtained silanol group-containing organosilicon compounds (i.e., a mixture of silanes and siloxanes) having an average degree of polymerization of more than 1 to less than 3, and especially up to 2.5.

EXAMPLE

Examples of the invention are given below by way of illustration and not by way of limitation.

Example 1

A 1000-ml flask equipped with a thermometer and stirrer and purged with nitrogen was charged with 370 g (3.08 mol) of dimethoxydimethylsilane and 110 g (6.11 mol) of water adjusted to pH 3.4 with hydrochloric acid, which formed a two-phase system. The two-phase mixture was vigorously agitated at room temperature. After 2 minutes of agitation, the mixture became homogeneous. The mixture was agitated for a further 13 minutes at room temperature. Then 1.0 g of a 35% aqueous solution of $KH_2PO_4/Na_2HPO_4$=1/1 (weight ratio) was added to the mixture to adjust it at pH 6.8, followed by 20 minutes of agitation. By vacuum stripping at 50° C. and 30 mmHg and filtration, 250.1 g of a colorless clear viscous liquid was collected.

The hydroxy group-containing siloxanes had an average degree of polymerization (DP) as reported in Table 1. The siloxanes were aged for 7 days at 25° C. The average degree of polymerization of the aged siloxanes is also reported in Table 1.

Example 2

Example 1 was repeated except that the phosphoric salt mixture $KH_2PO_4/Na_2HPO_4$=1/1 (weight ratio) was changed to $NaH_2PO_4/Na_2HPO_4$=1/1 (weight ratio).

Examples 3 to 8

Example 1 was repeated except that the reaction conditions were changed as shown in Table 1.

Comparative Example 1
(Neutralizing Agent Omitted)

A 1000-ml flask equipped with a thermometer and stirrer and purged with nitrogen was charged with 370 g (3.08 mol) of dimethoxydimethylsilane and 110 g (6.11 mol) water adjusted to pH 3.4 with hydrochloric acid, which formed a two-phase system. The two-phase mixture was vigorously agitated at room temperature. After 2 minutes of agitation, the mixture became homogeneous. By vacuum stripping at 50° C. and 30 mmHg and filtration, 240.7 g of a colorless clear viscous liquid was collected.

The average DP of the product as synthesized and the product aged for 7 days at 25° C. are reported in Table 2.

Comparative Example 2
(Neutralized with MgO)

A 1000-ml flask equipped with a thermometer and stirrer and purged with nitrogen was charged with 370 g (3.08 mol)

of dimethoxydimethylsilane and 110 g (6.11 mol) of water adjusted to pH 3.4 with hydrochloric acid, which formed a two-phase system. The two-phase mixture was vigorously agitated at room temperature. After 2 minutes of agitation, the mixture became homogeneous. The mixture was agitated for a further 13 minutes at room temperature. Then 0.0030 g of magnesium oxide was added to the mixture, which was agitated for 30 minutes for neutralization. By vacuum stripping at 50° C. and 30 mmHg and filtration, 241.1 g of a colorless clear viscous liquid was collected.

The average DP of the product as synthesized and the product aged for 7 days at 25° C. are reported in Table 2.

Comparative Example 3

Comparative Example 2 was repeated except that $Ca(OH)_2$ was used as the neutralizing agent.

TABLE 1

| Example | Mono-alkali metal phosphate (A) | Di-alkali metal phosphate (B) | A/B | pH | DP as synthesized | DP as aged |
|---|---|---|---|---|---|---|
| 1 | $KH_2PO_4$ | $Na_2HPO_4$ | 1 | 6.8 | 2.05 | 2.20 |
| 2 | $NaH_2PO_4$ | $Na_2HPO_4$ | 1 | 6.8 | 2.11 | 2.21 |
| 3 | $NaH_2PO_4$ | $Na_2HPO_4$ | 1.5 | 6.9 | 2.15 | 2.37 |
| 4 | $NaH_2PO_4$ | $Na_2HPO_4$ | 2 | 6.9 | 2.14 | 2.40 |
| 5 | $NaH_2PO_4$ | $Na_2HPO_4$ | 0.5 | 6.7 | 2.15 | 2.18 |
| 6 | $NaH_2PO_4$ | $Na_2HPO_4$ | 0.25 | 6.4 | 2.10 | 2.16 |
| 7 | $NaH_2PO_4$ | — | — | 6.0 | 2.10 | 2.40 |
| 8 | — | $Na_2HPO_4$ | — | 7.3 | 2.15 | 2.44 |

TABLE 2

| Comparative Example | Neutralizing agent | pH | DP as synthesized | DP as aged |
|---|---|---|---|---|
| 1 | none | — | 3.20 | 4.15 |
| 2 | MgO | 6.8 | 3.14 | 3.57 |
| 3 | $Ca(OH)_2$ | 7.0 | 3.02 | 3.52 |

According to the method of the invention, low molecular weight, silanol-containing organopolysiloxanes are readily obtained, and the resulting silanols remain stable during storage. As compared with the products of Examples, the organopolysiloxanes obtained by the methods of Comparative Examples have a long chain length due to condensation reaction between silanol groups and experience a substantial change of chain length with time.

There has been described a method capable of effectively producing hydroxyl (or silanol) group-containing organosilicon compounds having a low average degree of polymerization at a low cost.

Japanese Patent Application No. 11-131645 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A method for preparing organosilicon compounds having silanol groups, comprising the steps of:

adding water adjusted to a pH of 1 to 5 to at least one diorganooxysilane of the formula $(R^1O)_aSiR_{4-a}$, wherein $R_1$ and R are independently substituted or unsubstituted monovalent hydrocarbon groups and "a" is an integer of 1 to 4, in an amount of 0.5 to 3 mol per mol of the organooxy group in the diorganooxysilane, mixing them, thus forming a hydrolyzed diorganooxysilane mixture, and adding a mono-alkali metal salt of phosphoric acid and/or a di-alkali metal salt of phosphoric acid to the mixture, thus forming an organosilicon compound of the formula $H(OSiR_2)_nOH$ wherein R is as defined above and "n" denoting the average degree of polymerization, is more 1 to less than 3.

2. The method of claim 1 wherein the mono-alkali metal salt of phosphoric acid and/or the di-alkali metal salt of phosphoric acid is added to the mixture so as to adjust the resulting system at pH 5 to 9.

3. The method of claim 1 wherein the water is adjusted to a pH of 3 to 4.5.

4. The method of claim 1 wherein the diorganooxysilane is a member selected from the group consisting of dimethoxydimethylsilane, diethoxydimethylsilane, phenylmethyldimethoxysilane, methylvinyldimethoxysilane, trimethylmethoxysilane, trimethylethoxysilane, methyltrimethoxysilane, methyltriethoxysilane, vinyltrimethoxylsilane, phenyltrimethoxysilane, and mixtures thereof.

5. The method of claim 1 wherein the water is added in an amount of 1 to 1.5 mol per mol of the organooxy group in the diorganooxysilane.

6. The method of claim 1 wherein the mixing step includes agitation.

7. The method of claim 1 wherein the phosphoric acid salt comprises a mixture of a mono-alkali salt selected from the group consisting of $KH_2PO_4$ and $NaH_2PO_4$ and a di-alkali salt selected from the group consisting of $K_2HPO_4$ and $Na_2HPO_4$.

* * * * *